United States Patent [19]
DeMichele et al.

[11] Patent Number: 5,769,827
[45] Date of Patent: Jun. 23, 1998

[54] SAFETY NEEDLE APPARATUS AND METHOD

[75] Inventors: Louis R. DeMichele; John L. DeMichele, both of Barrington; Michael B. McDonald, Mundelein, all of Ill.

[73] Assignee: Safeguard Needle International, Inc., Palatine, Ill.

[21] Appl. No.: 823,830

[22] Filed: Mar. 25, 1997

Related U.S. Application Data

[63] Continuation of Ser. No. 296,329, Aug. 25, 1994, abandoned.

[51] Int. Cl.$^6$ .................................................. A61M 5/00
[52] U.S. Cl. ........................... 604/263; 604/164; 604/198
[58] Field of Search ..................................... 604/263, 198, 604/158–164, 174, 177, 168, 171, 195

[56] References Cited

U.S. PATENT DOCUMENTS

| | | | |
|---|---|---|---|
| 4,573,975 | 3/1986 | Frist et al. ................................. | 604/192 |
| 4,778,453 | 10/1988 | Lopez ....................................... | 604/110 |
| 4,834,718 | 5/1989 | McDonald . | |
| 4,846,805 | 7/1989 | Sitar ......................................... | 604/165 |
| 4,846,811 | 7/1989 | Vanderhoof ............................. | 604/263 |
| 4,850,996 | 7/1989 | Cree ......................................... | 604/198 |
| 4,872,552 | 10/1989 | Unger ....................................... | 206/365 |
| 4,944,725 | 7/1990 | McDonald . | |
| 5,088,988 | 2/1992 | Talonn et al. ............................ | 604/198 |
| 5,407,431 | 4/1995 | Botich et al. ......................... | 604/164 X |
| 5,474,534 | 12/1995 | Schlitt .................................. | 604/164 X |

*Primary Examiner*—John D. Yasko
*Attorney, Agent, or Firm*—McAndrews, Held & Malloy, Ltd.

[57] ABSTRACT

Disclosed is a safety catheter that automatically sheaths the needle upon withdrawal of the needle from a patient. The catheter can include a plunger for drawing a vacuum to draw blood or alternatively may delete the plunger and use nearly identical components with the addition of a blocking plug. The catheter also includes a cap/re-cap device that provides additional sheathing of the needle during assembly, shipping, and use of the needle. It also includes raised indicia that serves as a trademark as well as a friction gripping surface. The catheter includes improved catheter hub mounting structure as well as strengthened ribbed areas for grasping during use of the catheter.

7 Claims, 3 Drawing Sheets

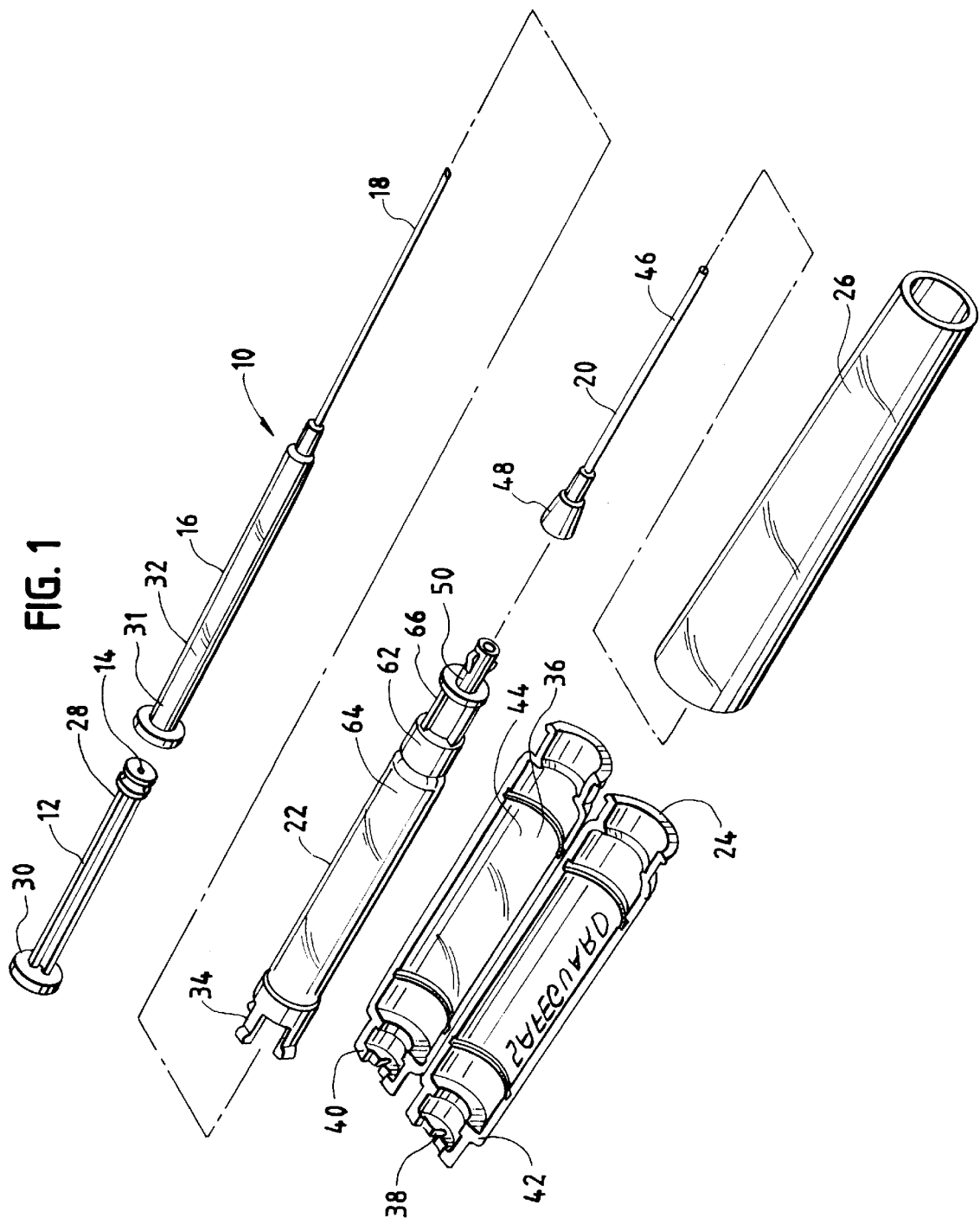

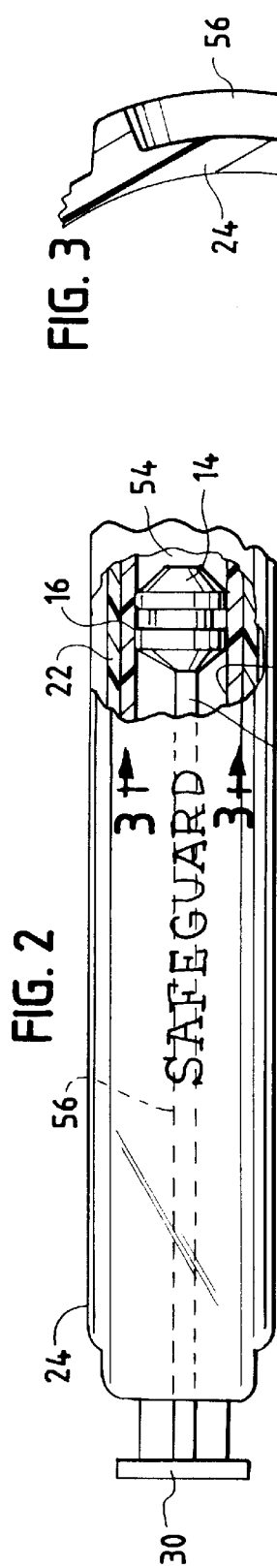
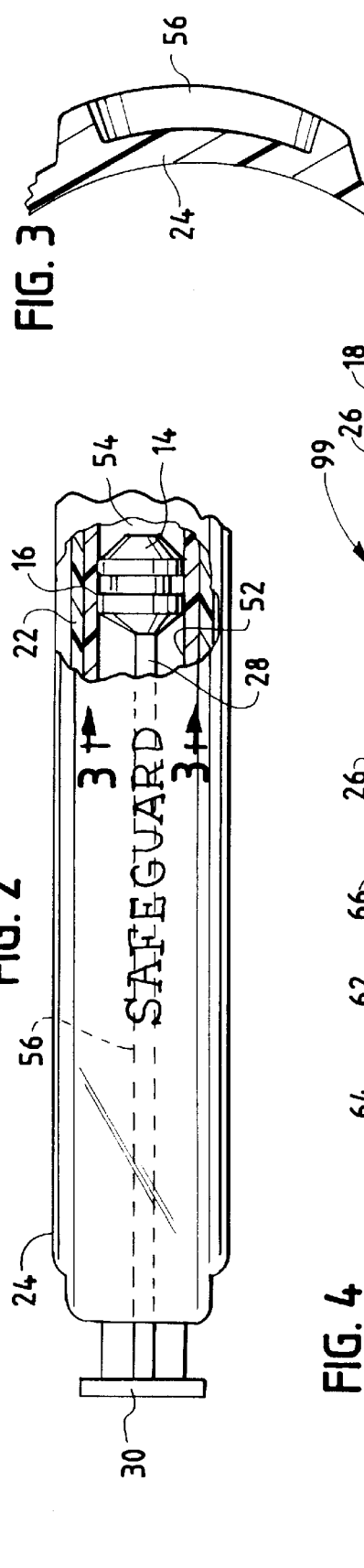
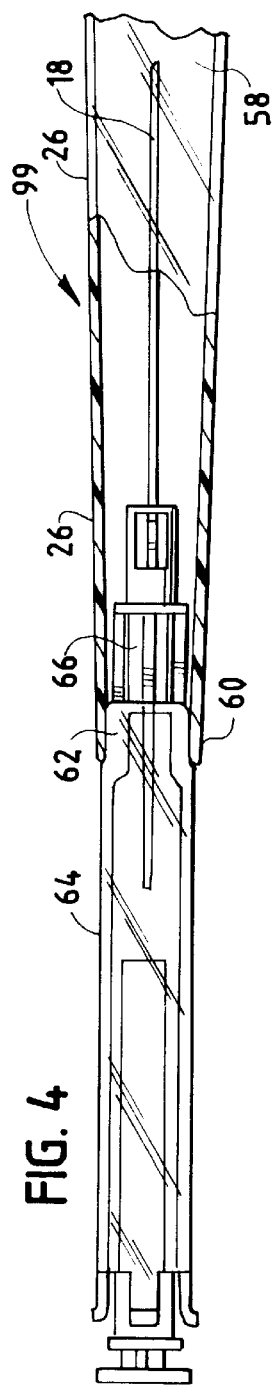
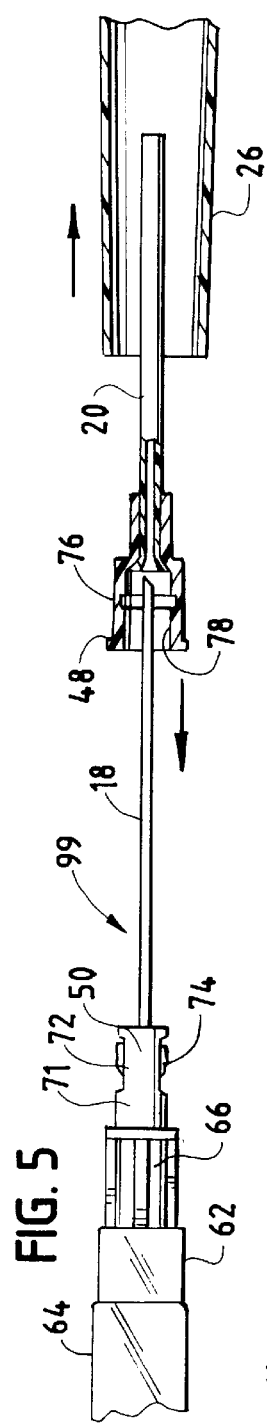
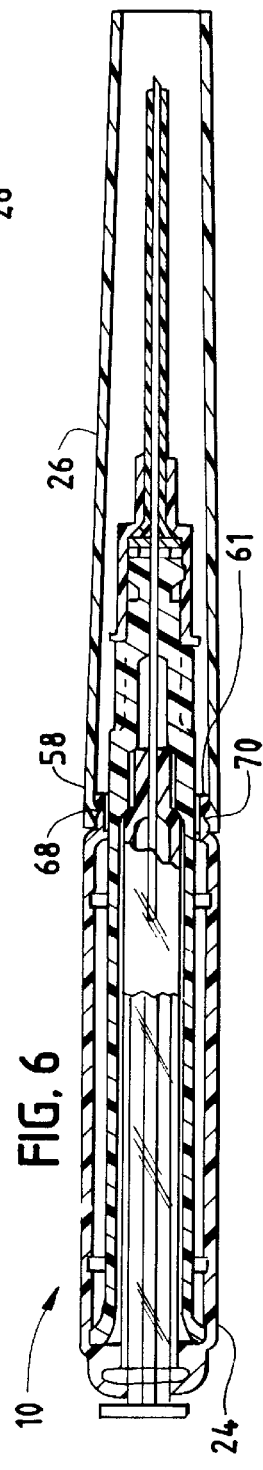

SAFETY NEEDLE APPARATUS AND METHOD

This is a continuation of application Ser. No. 08/296,329 filed Aug. 25, 1994 now abandoned.

BACKGROUND

A. Field of the Invention

This invention relates to safety needles of the type used to puncture the skin of patients. More particularly, this invention relates to intravenous catheters that protect the needle both before use and upon withdrawal from a patient.

B. Prior Art

Safety needles and catheters are old in the art. For example, safety catheters are disclosed in: (1) U.S. Pat. No. 4,834,718 ("the '718 patent") issued on May 30, 1989, to Michael McDonald; and (2) U.S. Pat. No. 4,944,725 ("the '725 patent"), issued on Jul. 31, 1990, to Michael McDonald. Mr. McDonald is one of the inventors of the present invention in this application.

The catheter in the '718 patent was the first catheter to provide convenient, reliable, economical, and automatic sheathing of the needle upon withdrawal of the needle from the patient. The '725 patent discloses improvements to Mr. McDonald's first patented structure in the '718 patent. The applicants hereby incorporate by reference the complete disclosures of the '718 and '725 patents.

The structures shown in the '718 and '725 patents were significant advances in the art. They included "flash back" chambers to determine, by relatively small sliding movement of an outer housing away from the catheter, whether the vein had been punctured sufficiently so that blood would flow through the catheter and needle into the flash back chamber where the blood could be seen at the back of the housing.

These prior structures, however, were not as effective in drawing blood into the flash back chamber when used on trauma patients with very low blood pressure. For these types of patients, the blood pressure of the patient can be too low to force blood through the catheter and needle into the flash back chamber in the housing. These prior art devices did not provide any way to draw a substantial vacuum in the housing in order to draw blood from the trauma patient into the flash back chamber when the needle and associated catheter penetrate the vein of the patient.

Other safety needles in the art have employed plungers penetrating the back of the needle housing to draw a vacuum in the housing. None of these prior art structures, however, have provided such a vacuum plunger for the McDonald safety needles shown in the '718 and '725 patents.

Another problem with the prior art safety catheters and needles is the lack of capping structure for complete capping of the entire needle and catheter during assembly, shipping, and pre-use handling. Thus, the prior art catheters and needles such as shown in the '718 and '725 patents provided an exposed needle during needle assembly and shipping. The needles are also exposed when removed from their packaging and prior to actual alignment for injection into the patient. This brings about risk of inadvertent needle sticks to manufacturers and needle operators, and subsequent inappropriate use of the same needles on patients. Accidental needle sticks can have dire consequences and have long been recognized as a great problem in the industry and, indeed, in society in general.

Needles such those shown in the '718 patent and '725 patent do sheath the needle upon withdrawal from the patient. This provides the great advantage of automatic sheathing and protection against needle sticks upon withdrawal, but it leaves the operator without the comfort of having taken any action on his or her own to cover the needle. Existing paramedics, nurses, and doctors in the field are often accustomed to the prior art devices that do not automatically sheath the needle upon withdrawal from the patient. These types of operators are often most comfortable with capping of the needle whether it is necessary or not. The prior safety catheters of the '718 and '725 patents, and other safety catheters in the prior art, did not provide any such additional capping feature, probably because it appears to be unnecessary. It is often necessary, in fact, however, since such a cap can put certain types of operators at ease and reduce their reluctance to use a safety needle such as that shown in the '718 and '725 patents.

The prior McDonald safety catheters of the '718 and '725 patents incorporated needle hub design that had a reduced and thin neck (shown as number 36 in FIG. 1 of the '718 patent). This neck is easy for the operator to grasp and hold in place with one hand while simultaneously, with the other hand, pulling back on the outer housing and thus automatically sheathing the needle within the needle housing. The reduced diameter neck is relatively weak, however, and may be subject to breakage when in use out in the field.

Finally, the prior McDonald safety catheter employed a cylindrical outer housing with a smooth, transparent plastic surface. The operator grasps and pushes and pulls on the this smooth surface when using the device out in the field. Although this cylindrical transparent design is particularly effective and reliable for a number of reasons, the operator's fingers can slip on the smooth surface, particularly when wet, and risk puncturing the patient incorrectly or at least not as accurately as desired. An incorrectly positioned needle puncture, which misses the vein or goes through it, can be painful and cause bleeding.

OBJECTS OF THE INVENTION

It is therefore an object of the present invention to develop a safety catheter and needle that develops a vacuum to draw blood into the flash back chamber when the needle is used on trauma patients having low blood pressure.

It is yet another object of the present invention to develop such a safety catheter and needle that provides protection against accidental needle sticks during needle and catheter assembly and shipping.

A further object is to provide a needle that also protects against accidental sticks upon opening of the needle package, removal of the needle from the package, and pre-use manipulation of the needle and catheter.

Another object is to provide a catheter and needle that also provides recapping structure to allow the operator to place an otherwise separate cap over the needle after its withdrawal from the patient.

Yet another object is to provide a single cap structure that provides both pre-use capping and post-withdrawal capping of the needle.

A still further object of the invention is to provide a catheter and needle housing that is less subject to slipping in the hands of a user while still being predominantly transparent and generally cylindrical for easy use and grasping.

Another object is to provide a safety catheter that is stronger, and less subject to accidental breakage in use, than prior catheters and needles.

An additional object is to provide a safety catheter that meets the prior objects while providing a safety catheter that is convenient, easy and economical to manufacture, assemble, and ship, slim yet sturdy, and easy to use and dispose of properly and safely.

There are other objects that will become apparent as the specification proceeds.

SUMMARY OF THE INVENTION

The foregoing objects and advantages are attained by our invention of an improved safety needle, preferably a catheter needle, that has an outer housing and an inner needle housing slidably mounted in the outer housing. The inner needle housing includes a catheter mounting end opposite the junction of the needle housing and the outer housing. Preferably, a removable cap, which is preferably frusto-conical, has one end mountable about the catheter mounting end and another end mountable on the outer housing. The cap can be mounted on the inner needle housing to protect against needle sticks during shipping of the inner needle housing and assembly of the catheter on the needle and the inner housing within the outer housing. The cap can then be reversed and mounted on the outer housing to protect against needle sticks during packaging, shipment, and pre-insertion manipulation of the catheter. Preferably, after withdrawal of the needle, the cap can be remounted on the outer housing to provide protection against accidental sticks after use of the needle and during disposal.

The outer housing may include a plunger penetrating the outer housing on the side of the outer housing opposite the needle. The plunger is slidably mounted in the outer housing to draw a vacuum within the outer housing. Alternatively, the plunger may be omitted and the plunger passage blocked with a plug.

The outer housing may also include a gripping friction surface which preferably results from embossing a trademark or suitable indicia on the outer surface of the outer housing. The inner needle housing may also include ribs or columns on the periphery of the needle housing to strengthen it while minimizing material use and providing grasping surfaces on the needle housing.

BRIEF DESCRIPTION OF THE DRAWINGS

The preferred embodiments of the applicants' invention are depicted in the following drawings in which:

FIG. 1 is an exploded isometric view of the major components of the preferred catheter embodiment having a plunger, a separable needle cap, and an embossed trademark/friction surface on the outer housing;

FIG. 2 is a partial plan view of the catheter needle of FIG. 1 after assembly and showing the plunger in partial cutaway within the housing;

FIG. 3 is a partial cross-sectional view through section line 3—3 of FIG. 2, showing the indicia embossing of the outer wall of the outer housing;

FIG. 4 is a cross-sectional view of the preferred plunger catheter showing the narrow end of the cap mounted on the inner needle housing to cover the needle during shipment and assembly;

FIG. 5 is a cross-sectional view of the preferred plunger catheter showing the cap being removed from the inner needle housing after assembly of the inner needle housing within the outer housing of the catheter;

FIG. 6 is a cross-sectional view of the preferred plunger catheter showing the cap inverted from the orientation of FIG. 5 and mounted on the outer housing to cover the catheter and needle during packaging, shipment, removal from the packaging by the user, and pre-use manipulation of the catheter;

Figure 7:
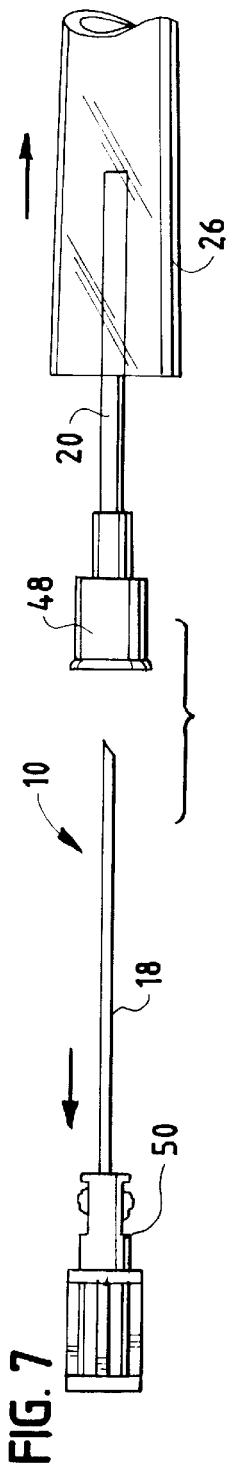
FIG. 7 is a cross-sectional view of the preferred plunger catheter showing removal of the cap from the outer housing prior to insertion of the needle and catheter into the patient.

This description of the preferred embodiment utilizes spacial orienting terms such as "back" and "outer." It is to be understood that these terms are used for convenience of description and not themselves limiting or requiring a particular location in space.

DETAILED DESCRIPTION OF THE PREFERRED EMBODIMENTS

Referring now to FIG. 1, the applicant's preferred plunger safety needle, generally 10, has a plunger rod 12 and plunger 14, a needle mounting cylinder 16, a needle 18, a catheter 20, an inner needle housing 22, an outer handle housing 24, and a cap 26. The plunger rod 12 consists of an "X" shaped plunger beam 28 extending perpendicularly from a planar plunger end cap 30. The plunger beam 28 slidably penetrates the open end 31 of a cylindrical flash back chamber 32 on the interior of the needle mounting cylinder 16; and the needle 18 is mounted on the end of the needle mounting cylinder 16 opposite the open end 31 of the flash back chamber 32.

The needle mounting cylinder 16 slidably penetrates an open passage 34 in the needle housing 22. In turn, the needle housing 22, the needle mounting cylinder 16, plunger rod 12, and plunger 14 are mounted within the generally cylindrical interior wall 36 o f the outer handle housing 24. The plunger beam 28 of the plunger rod 12 slidably penetrates and abuts the "X" shaped plunger passage 38 cooperatively provided by the mating upper 40 and lower 42 halves of the handle housing 24 when sonically welded together with the needle housing 22 and the associated structure assembled within the handle housing 24.

The plunger rod 12 is thus slidably mounted in the plunger passage 38 to slidably penetrate the cylindrical flash back chamber 32 within the needle mounting cylinder 16. In turn, the substantially cylindrical needle housing 22 slidably penetrates a housing passage 44 provided within the interior wall 36 of the handle housing 24.

The catheter 20 has a skin penetration tube 46 coaxially extending from an expanded catheter hub 48. The catheter hub 48 mounts on the catheter mount 50 extending from the needle housing 22, and the cap 26 is mountable on the needle housing 22 or the handle housing 24 as explained below.

Referring now to FIG. 2, the plunger beam 28 has a resilient plunger 14 mounted within and slidably abutting the interior wall 52 of the needle mounting cylinder 16. Thus, when the plunger cap 30 is drawn away from the handle housing 24 and air cannot enter through the needle 18 (not shown in FIG. 2) into the interior vacuum space 54 within the needle mounting cylinder 16, the plunger 14 slides within the mounting cylinder 16 in the same direction and simultaneously draws a vacuum in the interior vacuum space 54. If the needle 18 has penetrated the vein of a patient (not shown) when the vacuum is drawn in the interior vacuum space 54, blood is urged to flow from the vein, through the needle, and into the vacuum space 54.

The outer surface of the handle housing 24 includes trademark indicia 56. With reference to FIG. 3, the indicia 56 projects from the outer surface of the housing 24. The raised indicia 56 not only can identify the product and convey information about the product 10 but also can provide a surface that is more likely to cause greater friction in the hands of a user and less likely to result in slippage when in use. This is particularly helpful in an emergency, when sweaty palms and other fluids, including blood, etc., may otherwise render the outer surface of the handle housing 24 quite slippery. The preferred indicia 56 are cut into the molds for the needle housing 24 so that the indicia 24 are included into the transparent housing 24 automatically when molded. Other surface alteration or scoring may also be utilized.

Referring now to FIG. 4, the cap 26 is frusto-conical and thus has a larger somewhat cylindrical end 58 opposite a narrower somewhat cylindrical end 60. The cap is made out of resilient material, and its narrower end 60 is mountable on the narrowed cap mounting hub 62 on the needle housing 22. The cap mounting hub 62 is intermediate the wider needle mounting housing central body 64 and the narrower raised column guard hub 66. When mounted on the hub 62, the cap 26 thus provides a protective shield around the needle 18 extending from the needle housing 22 when the needle mounting cylinder 16 is placed within the needle housing 22 as shown in FIG. 1. In this manner, the partial needle assembly 99 (consisting of the needle housing 22, needle mounting cylinder 16, needle 18, and cap 26) can be shipped or moved from one assembling or manufacturing area to another with significantly reduced risk of any accidental needle stick to an assemblers, handlers, etc.

With reference now to FIG. 5, the cap 26 is readily removed by an operator. The partial needle assembly 99 can then be further assembled into the handle housing 24 as shown in FIG. 1.

With the cap 26 removed, the next manufacturer can install the catheter 20 by sliding it over the needle 18 so that the catheter hub 48 mounts on the catheter mount 50. The catheter mount 50 has a cylindrical mounting body 71 with diametrically opposed catheter hub engaging arms 72, 74 extending radially outwardly from the mounting body 71. The catheter hub 48 has a radially extending detent or undercut 76 penetrating the cylindrical interior wall 78 of the catheter hub 48.

Referring now to FIG. 6, the catheter hub 48 mounts on the catheter mount 50 and is retained in place on the mount 50 by the radially extending arms 72, 74, which penetrate the radially extending undercut 76 in the catheter hub 48. The catheter hub 48 is made of resilient material and is held in place by the arms 72, 74 until the operator forces the catheter 20 off of the mount 50 until it is fully separated from the needle housing 22.

Still referring to FIG. 6, the larger end 58 of the cap 26 has an internal radial rib or lip 68. The handle housing 24 has a mating radial detent 70 on the needle end 61 of the handle housing 24 opposite the plunger end cap 30 (not shown in FIG. 6). The larger end 58 of the cap 26 is mounted on the needle end 61 so that the cap's internal rib 68 abuts the radial detent 70 in the housing 24. In this manner, the protective cap 26 is mounted on the handle housing 24 to extend from the housing 24 and surround the needle 18 and catheter 20. The protective cap 26 once again provides a protective sheath around the needle 18 and catheter 20 to minimize accidental needle sticks during (i) further packaging, shipment, and handling of the packaging, (ii) opening of the packaging, and (iii) pre-use manipulation of the catheter 10 prior to actual use to puncture the skin of a patient.

Referring now to FIG. 7, when the operator is ready to use the needle 18 and catheter 20, the cap 26 may be pulled off of the handle housing 24 (not shown). The operator may now insert the needle 18 and catheter 20 into the patient as described in the '718 and '725 patents.

Figure 8:
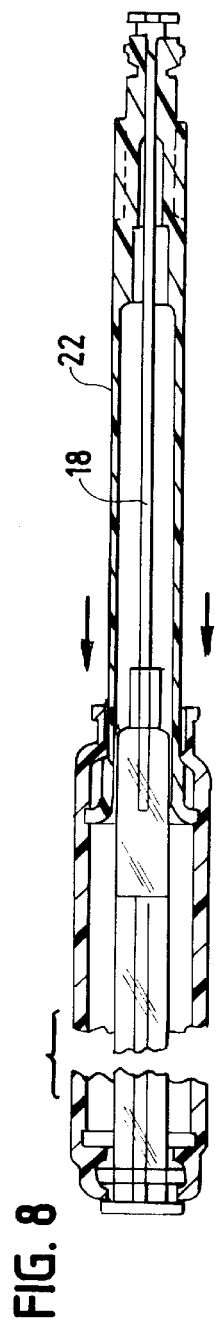
FIG. 8 is a cross-sectional view of the preferred plunger catheter showing the withdrawal of the needle from the patient and automatic sheathing of the needle within the inner needle housing.

Referring back to FIG. 5, the raised column guard hub 66, which is exposed upon removal of the cap 26, provides significant strength with minimum material between the cap mounting hub 62 and catheter mounting hub 50 on the needle housing 22. The operator can readily grasp this area 66 of the needle housing to hold the housing 22 when withdrawing the needle 18 from the patient (not shown). In this operation, the handle housing (not shown in FIG. 5) can be drawn away from the patient with one hand while grasping the guard hub 66 and holding it in place as (i) the needle 18 is drawn out of the patient, (ii) the mounting hub 50 separates from the catheter hub 48 as shown in FIG. 7, (iii) the needle 18 slides out of the catheter 20 as also shown in FIG. 7, and (iv) the needle 18 is drawn into the needle housing 22 as shown in FIG. 8. This operation is described in greater detail in the '718 and '725 patents.

Figure 9:
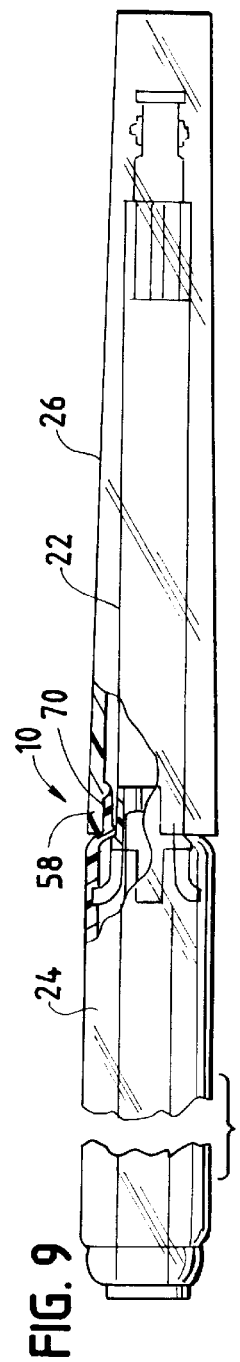
FIG. 9 is a cross-sectional view of the preferred plunger catheter showing the cap mounted once again on the outer housing to further protect the inner housing and needle within the inner housing.

Now that the operator has completed use of the needle 18, the operator can, as shown in FIG. 9, slide the large end 58 of the cap 26 over the needle housing 22 to yet again engage the radial detent 70 and secure the cap 26 on the handle housing 24. The same cap 26 thus provides yet another level of protection against subsequent needle sticks. This cap-remounting procedure also provides the clinician, particularly one who is accustomed to manual capping of needles after use, with a greater level of comfort and security in using the safety needle 10. It also reduces the likelihood that the cap 26 will be left behind on the street or any other accident or trauma location.

Figure 10:
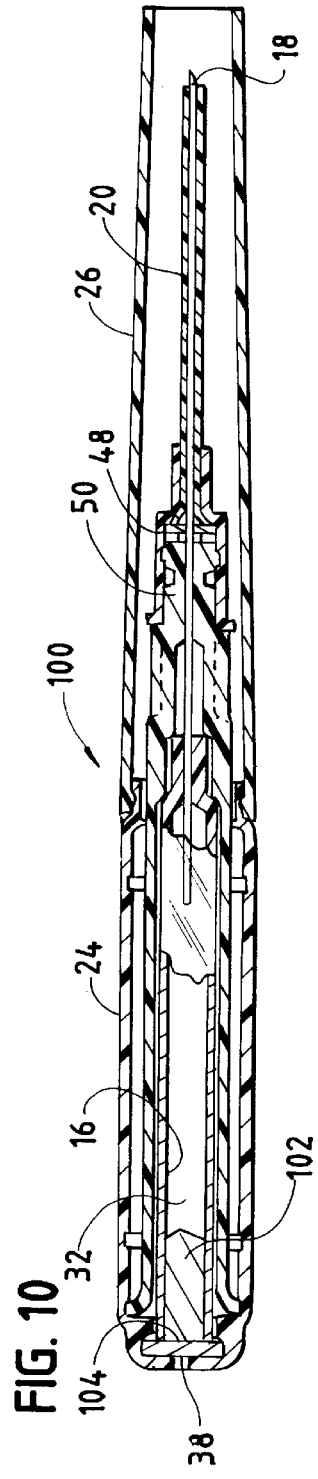
FIG. 10 is a cross-section view of the preferred catheter without the plunger and with a flash back plug abutting and thus blocking the plunger passage in the back of the outer housing.

Referring now to FIG. 10, the cap 26, indicia 56, (FIG. 1) on the housing 24, mounting hub 50, and catheter hub 48 described above may also be used on a safety needle not having a plunger at all. This type of catheter is preferably for use with patients having sufficient blood pressure. This non-plunger needle 100 has a resilient plug 102 mounted within the mounting cylinder 16 to extend therefrom and abut the generally planar interior end 104 of the needle housing 24. The plug 102 thus abuts the "X" shaped plunger passage 38 and prevents the flow of blood from the flash back chamber 32 through the plunger passage 38.

The protective cap 26, plunger rod 12 and catheter hub 48 are preferably made from polypropylene. The plug 102 is made from rubber, and the handle housing 24 and needle mount 16 are made from high impact polystyrene. The needle is made of steel. The catheter 20 is made from radiopaque Teflon, and the needle housing 22 is made from ploycarbonate.

It can thus be seen that the applicants have invented a safety catheter and needle that is safer than prior art catheters and needles and yet convenient, economical, and easy to assemble and manufacture. It provides numerous significant advantages over the prior art, and it does so at minimal cost.

While in the foregoing the applicants have described their preferred embodiments, it is to be understood that the scope of the invention is to be determined by reference to the following claims.

What is claimed is:

1. An improved needle apparatus comprising in combination:
   A. a first housing having a first end;
   B. a needle secured to said first housing, extending beyond said first end, and having a point which can be injected into a patient;
   C. a second housing movably captured by said first housing, said second housing having a first end and an opposite end; and
   D. a removable cap adapted for engaging the first end of said first housing to provide a sheath for said needle, and also adapted for engaging the first end of said second housing to provide a sheath for said needle;
   wherein said first housing and needle are manually movable, with respect to said second housing, between:
      a needle exposing position at which said needle point is outside said second housing, and
      needle sheathing position at which said point is withdrawn into said second housing after said needle is fully withdrawn from a patient to prevent an accidental needle stick.

2. The needle apparatus of claim 1, further comprising a catheter, wherein said needle extends into said catheter when in said needle exposing position and is outside said catheter when in said needle sheathing position.

3. The needle apparatus of claim 1, wherein the opposite end of said second housing is disposed within at least a portion of said first housing.

4. The needle apparatus of claim 1, wherein said cap has a first end adapted for engaging the first end of said first housing to provide a sheath for said needle and a second end.

5. The needle apparatus of claim 1, wherein said cap has a first end and a second end, wherein said second end is adapted for engaging the first end of said second housing to provide a sheath for said needle.

6. The needle apparatus of claim 1, wherein said cap has a first end adapted for engaging the first end of said first housing to provide a sheath for said needle and a second end adapted for engaging the first end of said second housing to provide a sheath for said needle.

7. The needle apparatus of claim 1, wherein said cap is one piece.

* * * * *